(12) United States Patent
Boutos

(10) Patent No.: US 6,785,577 B2
(45) Date of Patent: Aug. 31, 2004

(54) ELECTRODE APPARATUS FOR STIMULATING PENILE, URETHRAL, AND ANAL TISSUE

(76) Inventor: David Boutos, 4950 Mountain Creek Dr., Las Vegas, NV (US) 89148

( * ) Notice: Subject to any disclaimer, the term of this patent is extended or adjusted under 35 U.S.C. 154(b) by 298 days.

(21) Appl. No.: 09/951,799

(22) Filed: Sep. 10, 2001

(65) Prior Publication Data

US 2003/0050683 A1 Mar. 13, 2003

(51) Int. Cl.⁷ .............................................. A61N 1/04
(52) U.S. Cl. ...................................... 607/143; 607/138
(58) Field of Search ................................ 607/115, 119, 607/122, 143, 139, 149, 153; 600/372, 382, 384

(56) References Cited

U.S. PATENT DOCUMENTS

| | | | | |
|---|---|---|---|---|
| 5,928,142 A | * | 7/1999 | Cartmell et al. | 607/153 |
| 6,151,527 A | | 11/2000 | Boutos | 607/138 |
| 6,246,915 B1 | | 6/2001 | Boutos | 607/143 |

OTHER PUBLICATIONS

Cambridge University Press Definition of "sheath", 2004.*

* cited by examiner

Primary Examiner—George R. Evanisko
(74) Attorney, Agent, or Firm—Jordan M. Meschkow; Lowell W. Gresham; Meschkow & Gresham, PLC

(57) ABSTRACT

An electrode apparatus (20) includes an electrode (22), an electrical contact (24), and a non-conductive sheath (26) surrounding a portion (44) of the electrical contact (24). The electrode (22) includes an interior passage (36) configured for the placement of electrolytic gel (88). Openings (38) are disposed along a length (28) of the electrode (22) and extend from the interior passage (36) to an exterior surface (34). The openings (38) facilitate the leakage of the electrolytic gel (88) from the interior passage (36) to the exterior surface (34) of the electrode (22) when the electrode apparatus (20) is in use. A rigid conducting dowel (62) and a conductive tubular member (60) are located in the non-conductive sheath (26). The portion (44) of the electrical contact (24) fits in an inner passage (68) of the member (60). Thus, the dowel (62) and the member (60) ensure electrical continuity between the electrical contact (24) and the electrode (22).

21 Claims, 6 Drawing Sheets

ELECTRODE APPARATUS FOR STIMULATING PENILE, URETHRAL, AND ANAL TISSUE

TECHNICAL FIELD OF THE INVENTION

The present invention relates to devices for applying electrical energy to living tissue. More particularly, the present invention relates to an apparatus for electrically stimulating penile and anal tissue.

BACKGROUND OF THE INVENTION

It is known that medical disorders such as diabetes, leukemia, anemia, X-ray exposure, and so forth can cause impotence in males. Furthermore, it is known that the application of electrical stimulation to penile tissue can cause erection where impotence may exist due to these physiological conditions or due to psychological conditions. Indeed, it is known that the application of electrical stimulation to penile, urethral, and anal tissue can induce orgasm, even where the subject has suffered damage to the nerves serving the sex organs.

The art is replete with various devices used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the penis, and to the skin and muscles inside the anus.

Rigid rings are useable for males where the application of electrical current to only a portion of penile tissue is sufficient to induce erection. However, due to the tremendously varying size of the penile tissue from rest to engorgement, the rigid ring may cause discomfort or pain to the user when the penis is engorged.

In males, the glans, or head of the penis, is highly sensitive to stimulation. Likewise, the corona, i.e., the ridge of flesh demarcating where the glans and the shaft of the penis join, is highly sensitive. Rigid rings that are typically worn along the shaft of the penis do not provide sufficient stimulation about the glans and the corona.

Internally worn insertable electrodes are desirable to stimulate and to induce orgasm. However, many of these prior art insertable electrodes are difficult to retain in the appropriate position, uncomfortable for prolonged wear due to rigid components, and hard to effectively clean.

In addition to the problems described above, the use of the prior art devices can cause discomfort, pain, and even injury to the users of the devices due to the development of hotspots. A hotspot is an area of intense heat and/or pain produced by a concentration of electrical energy at a contact point of the electrode device. This hotspot can be due to insufficient or unevenly distributed quantities of lubricant resulting in poorly distributed electrical contact between the electrode and the skin. Hotspots are particularly painful and consequently, highly undesirable on the sensitive tissues inside and around the penis and inside the anus.

It would be highly advantageous, therefore, to remedy the foregoing and other deficiencies inherent in the prior art.

SUMMARY OF THE INVENTION

Accordingly, it is an advantage of the present invention to provide an improved apparatus for the application of electrical stimulation to penile, urethral, and anal tissue.

Another advantage of the present invention is to provide an electrode apparatus that can induce erection and orgasm.

A further advantage of the present invention is that an electrode apparatus is provided for the application of electrical stimulation to the penile tissue that is comfortable to wear during penile engorgement.

Yet another advantage of the present invention is that an electrode apparatus is provided that enables an even distribution of electrical contact between the apparatus and the penile, urethral, and anal tissue.

The above and other advantages of the present invention are carried out in one form by an electrode apparatus that includes an electrode exhibiting a length, and having first and second ends located at opposite ends of the length, an exterior surface, an interior passage, and openings disposed along the length and extending from the exterior surface to the interior passage. The electrode apparatus further includes an electrical contact and a non-conductive sheath surrounding a portion of the electrical contact and retaining the electrical contact in electrical communication with the electrode.

The above and other advantages of the present invention are carried out in another form by an electrode apparatus that includes an electrode exhibiting a length, and having first and second ends located at opposite ends of the length, and an aperture located on the length. A rigid conductive dowel is disposed in and extends from the aperture, and a conductive tubular member is bonded to the electrode about the aperture and surrounds the rigid conductive dowel. The electrode apparatus further includes an electrical contact and a non-conductive sheath having a bore. The bore has a first interior portion exhibiting a first inner diameter, and a second interior portion exhibiting a second inner diameter that is less than the first inner diameter. The first and second interior portions are axially aligned and contiguous. The conductive tubular member is press-fit into the first interior portion, and an end of the electrical contact is inserted through the second interior portion and into the first interior portion for press-fit into the conductive tubular member. The non-conductive sheath retains the electrical contact in electrical communication with the electrode via the conductive tubular member and the rigid conductive dowel.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
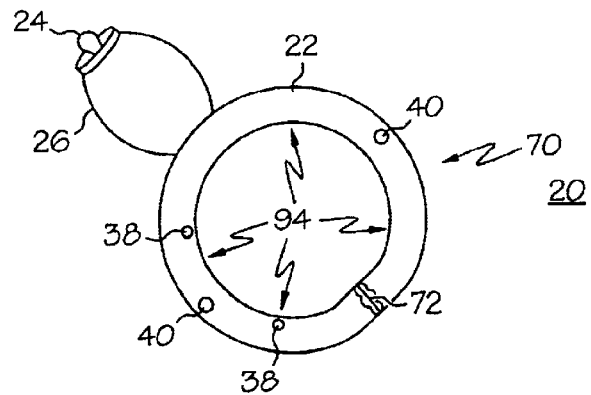
FIG. 1 shows a perspective view of an electrode apparatus in accordance with a preferred embodiment of the present invention.
Figure 2:
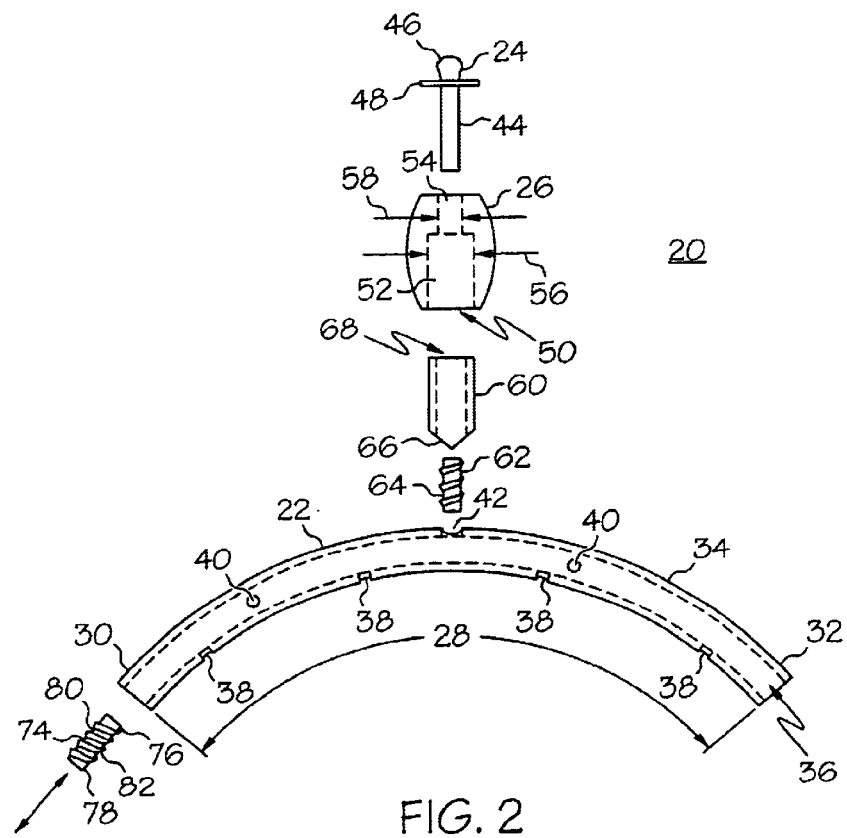
FIG. 2 shows an exploded side view of the electrode apparatus of FIG. 1.

Turning now to the drawings in which like reference characters indicate corresponding elements throughout the several views, attention is first directed to FIGS. 1–2 where an electrode apparatus 20 is shown. FIG. 1 shows a perspective view of electrode apparatus 20 in accordance with a preferred embodiment of the present invention. FIG. 2 shows an exploded side view of electrode apparatus 20.

Electrode apparatus 20 includes an electrode 22, an electrical contact 24, and a non-conductive sheath 26. Electrode 22 is in the form of a tube and exhibits a length 28, and a first end 30 and a second end 32 located at opposite ends of length 28. Electrode 22 has an exterior surface 34 and an interior passage 36, represented by hidden lines. Openings 38 are disposed along length 28 and extend from exterior surface 34 to interior passage 36. In addition, holes 40 and an aperture 42 are disposed along length 30 and extend from exterior surface 34 to interior passage 36.

Electrode 22 is desirably fabricated from an elastomeric material such as silicone, fluorolastomer, or neoprene for comfort and cleanability. Electrode 22 is made conductive along length 28 by embedding carbon particles in the elastomeric material during fabrication. Alternatively, electrode 22 may be fabricated from other pliable conductive materials such as conductive ceramic, metals, twisted or braided wires, and such.

Electrical contact 24 is desirably fabricated from a rigid conductive material, such as brass. Electrical contact 26 has an insert end 44, a connection end 46, and a collar 48 interposed between insert end 44 and connection end 46.

Non-conductive sheath 26 is desirably fabricated from a rigid non-conductive material such as ceramic, plastic, or resin-based materials, for example, Delrin. Non-conductive sheath 26 includes a bore 50 having a first interior portion 52 and a second interior portion 54 that are axially aligned and contiguous. First interior portion 52 exhibits a first inner diameter 56 and second interior portion 54 exhibits a second inner diameter 58 that is less than first inner diameter 56.

Electrode apparatus 20 further includes a conductive member 60 and a rigid conductive dowel 62. Conductive member 60 is in the form of a tube and is desirably fabricated from an elastomeric material such as silicone, fluorolastomer, or neoprene made conductive by embedding carbon particles in the elastomeric material during fabrication. Rigid conductive dowel 62 may include threads 64 or barbs and is desirably fabricated from a rigid conductive material, such as brass.

With particular reference to FIG. 2, during assembly rigid dowel 62 is directed through aperture 42 of electrode 22. Conductive tubular member 60 is installed over dowel 62 such that dowel 62 is seated in an inner passage 68 of conductive tubular member 60. Conductive tubular member 60 is then bonded to electrode 22 about aperture 42. In a preferred embodiment, conductive tubular member 60 is bonded to electrode 22 using a cyanoacrylate adhesive. Cyanoacrylate adhesive provides a durable, secure coupling between metal, such as brass, and elastomeric materials, such as silicone. Conductive tubular member 60 includes an angular cut 66 that enables member 60 to seat securely against the curved surface of electrode 22.

After conductive tubular member 60 is bonded to electrode 22, non-conductive sheath 26 is slid over member 60 and conductive tubular member 60 is press-fit into first interior portion 52 of sheath 26. Non-conductive sheath 26 may also be glued onto electrode 22 about aperture 42 and onto member 60 for a more secure connection. Insert end 44 of electrical contact 24 is then inserted through second interior portion 54 and into contact with conductive tubular member 60 in second interior portion 52. In particular, insert end 44 slides into inner passage 68 of conductive tubular member 60. Conductive tubular member 60 and rigid conductive member 62 form a path for electrical communication, thus ensuring electrical continuity between electrical contact 24 and electrode 22. In addition, the inclusion of rigid conductive dowel 62 increases the strength and durability at the junction of non-conductive sheath 26 and electrode 22.

In a preferred embodiment, electrode apparatus 20 includes both conductive tubular member 60 and rigid conductive dowel 62. However, in a first alternative embodiment, conductive tubular member 60 may have a solid core and may be rigid. In such a scenario, this solid core conductive member would insert directly into aperture 42. In addition, insert end 44 of electrical contact 24 would contact this solid core conductive member in second interior portion 52 of non-conductive sheath 26.

In a second alternative embodiment, conductive tubular member 60 is replaced by an insulated wire with a small contact section of wire extending beyond the insulation (not shown). In this scenario, this insulated wire would insert directly into aperture 42, until the small contact section of the wire is in contact with the inner conductive electrode. Then a standard button or banana-type plug may be used in place of electrical contact 24 (also not shown).

It should also be understood that electrode 22 may be a solid core electrode without openings 38 and holes 40. Thus, aperture 42 would be an opening in the solid core electrode 22 into which rigid conductive member may be inserted and secured.

Electrode apparatus 20 includes a coupling for attaching first end 30 of electrode 22 to second end 32 of electrode 22 to retain electrode 22 in a ring-shaped configuration 70. As shown in FIG. 1, the coupling is an adhesive 72 for non-removable attachment of first end 30 to second end 32. In a preferred embodiment, adhesive 72 is cyanoacrylate adhesive for enabling a secure and durable bond between first and second ends 30 and 32, respectively.

An alternative coupling is shown in FIG. 2. The alternative coupling is an insert 74 that allows for removable attachment of first end 30 to second end 32. Insert 74 has a first insert end 76 and a second insert end 78. To retain electrode 22 in ring-shaped configuration 70, first insert end 76 is positioned in interior passage 36 of electrode 22 at first end 30 and second insert end 78 is positioned in interior passage 36 at second end 32. Insert 74 has an exterior surface 80 made uneven through the inclusion of threads 82. Threads 82 provide surface resistance between insert 74 and interior passage 36 of electrode 22 to provide a non-slipping, but impermanent, union between first and second ends 30 and 32, respectively. Those skilled in the art will recognize that other structures, such as barbs, may be employed for providing surface resistance.

In operation, first and second ends 30 and 32 may be trimmed to the appropriate length so that when electrode 22 is placed in ring-shaped configuration 70, electrode apparatus 20 comfortably and securely fits to the particular anatomy upon which it will be worn. For example, when electrode apparatus 22 is trimmed to the appropriate length and in ring-shaped configuration 70, electrode apparatus 20 can be worn about the shaft of the penis or about the scrotum.

Electrode apparatus 20 is readily assembled and disassembled without the use of tools. In addition, the simplicity of the coupling between the components allows electrode apparatus 20 to be easily disassembled for cleaning and replacement of parts.

Although electrode apparatus 20 is shown having a single electrical contact, another configuration may include a pair of electrical contacts. For example, an electrode apparatus in a ring-shaped configuration may include two electrical contacts, each of which is electrically isolated from the other so that different electrical stimulation may be provided to different sides of the shaft of the penis.

Figure 3:
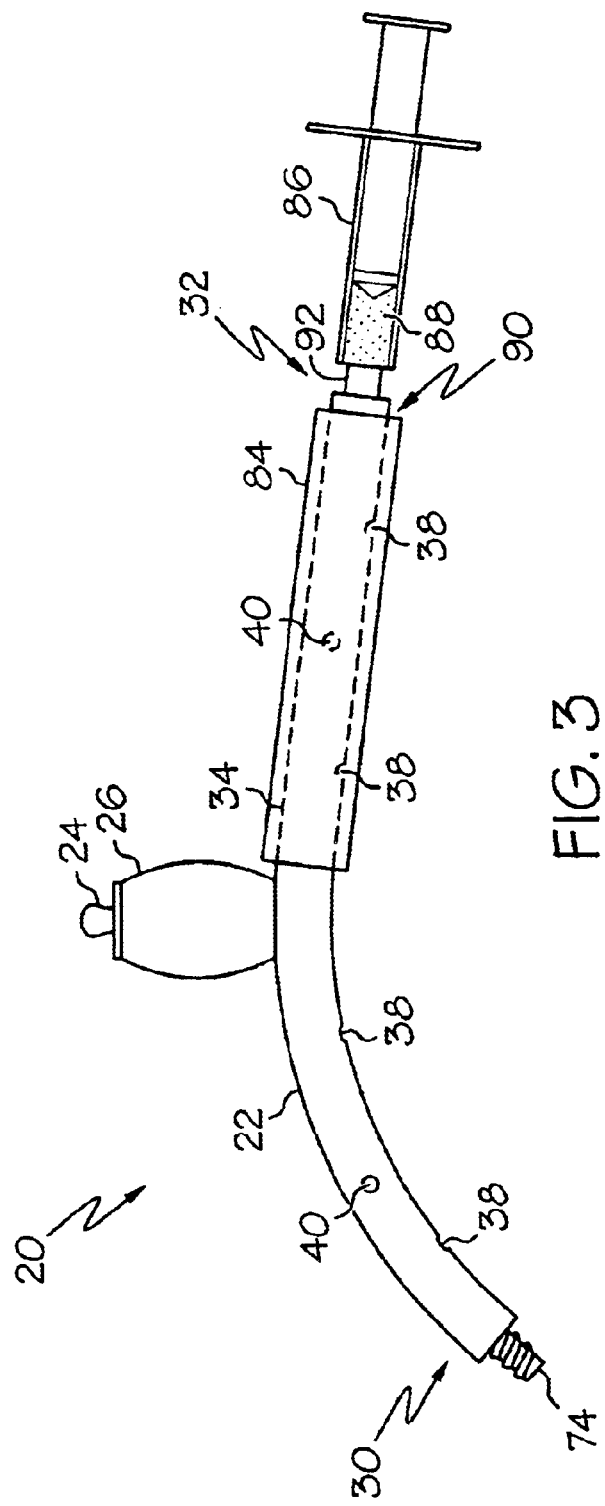
FIG. 3 shows a perspective view of the electrode apparatus of FIG. 1 with an encapsulating tube and an injection element.

FIG. 3 shows a perspective view of electrode apparatus 20 with an encapsulating tube 84 and an injection element 86 containing a quantity of electrolytic gel 88. In a preferred embodiment, encapsulating tube 84 is fabricated from a clear plastic material, the usefulness of which will become apparent below. Injection element may be a syringe having a hollow barrel filled with electrolytic gel 88 and a plunger that when activated forces gel 88 out of the barrel. Those skilled in the art will recognize that other instruments may operate satisfactorily as injection element 86 in lieu of a syringe.

Electrolytic gel 88 provides both lubrication and conductivity when electrode apparatus 20 is in use, as discussed below. In a preferred embodiment, electrolytic gel 88 is a material commonly employed for conductive measurement, such as EKG gel or ultrasound gel, that contains a suspension of fine, metallic, particulate materials such as silver, carbon particles, and the like.

Prior to arranging electrode 22 in ring-shaped configuration 70 (FIG. 1), encapsulating tube 84 is temporarily placed about exterior surface 34 of electrode 22. Encapsulating cylinder 84 is desirably tubular and sized to fit over electrode 22 so that an open end 90 of encapsulating cylinder 84 is positioned about either of first and second ends 30 and 32, respectively. FIG. 3 shows open end 90 of encapsulating cylinder 84 positioned about second end 32 for clarity of illustration.

Interior passage 36 (FIG. 2) of electrode 22 is configured for placement of electrolytic gel 88. Accordingly, an outlet 92 of injection element 86 is positioned at open end 90 and electrolytic gel 88 is forced through second end 32 of electrode 22 and into interior passage 36 of electrode 22. Encapsulating cylinder 84 blocks a number of openings 38 and holes 40 to largely prevent electrolytic gel 88 from leaking out of openings 38 and holes 40 during the injection process. However, the translucency of encapsulating cylinder 84 enables a user to visually inspect electrode 22 and discontinue forcing electrolytic gel 88 into interior passage 36 when gel 88 can be seen through openings 38 and holes 40.

Insert 74 is then removed from first end 30, encapsulating cylinder 84 is placed into position, and a second quantity of electrolytic gel 88 is injected into the other half of electrode 22. Alternatively, two encapsulating cylinders 84 may be utilized at the same time to surround length 28 (FIG. 2) of electrode 22. As such, electrolytic gel 88 may be injected into interior passage 36 (FIG. 2) of the entire length 28 of electrode 22 from second end 32.

Following the injection of electrolytic gel 88 into interior passage 36, encapsulating cylinder 84 is removed from electrode 22, and electrode 22 is placed in ring-shaped configuration 70. Alternatively, when electrode apparatus is retained in ring-shaped configuration 70 using adhesive 72 (FIG. 1), electrolytic gel 88 may be injected into interior passage 36 using one of openings 38. Openings 38 facilitate a leakage of electrolytic gel 88 from interior passage 36 to exterior surface 34 when in use. Moreover, when electrode is oriented in ring-shaped configuration, openings are arranged on an inside circumference 94 (see FIG. 1) which is the skin contacting side of electrode apparatus 20. The leakage of electrolytic gel 88 provides viscosity and conductivity for minimizing the electrical resistance between the skin and exterior surface 34 of electrode 22. As such, electrical energy is evenly distributed along electrode 22 and the development of a hotspot on the skin is largely avoided.

Figure 4:
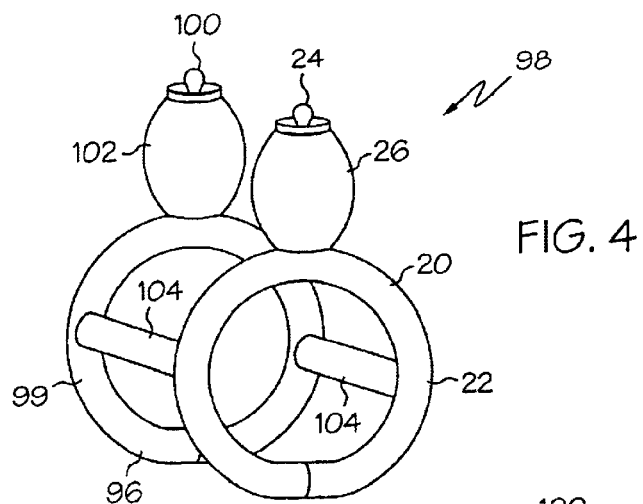
FIG. 4 shows a perspective view of the electrode apparatus of FIG. 1 coupled with a second electrode apparatus to form a double-ring configuration.
Figure 5:
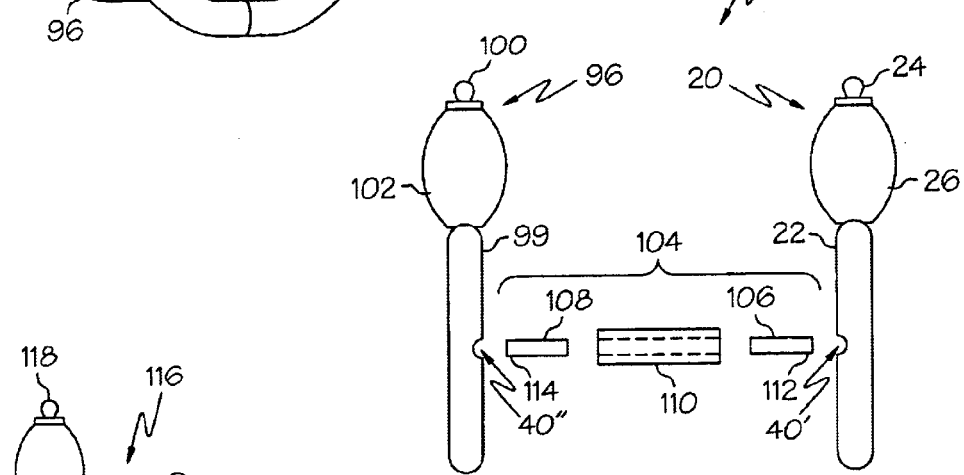
FIG. 5 shows an exploded side view of the double-ring configuration of FIG. 4.

Referring to FIGS. 4–5, FIG. 4 shows a perspective view of electrode apparatus 20 coupled with a second electrode apparatus 96 to form a double-ring configuration 98. FIG. 5 shows an exploded side view of double-ring configuration 98. It may be desirable to provide electrical stimulation at more than one location along, for example, the shaft of the penis. Accordingly, double-ring configuration 98 of electrode apparatus 20 enables electrical stimulation at more than one location.

Second electrode apparatus 96, includes a second electrode 99, a second electrical contact 100, and a second non-conductive sheath 102. Second electrode apparatus 96 is fabricated similarly to electrode apparatus 20. Thus, the teachings of electrode apparatus 20, including electrical contact 24, non-conductive sheath 26, conductive tubular member 60, rigid conductive member 62, and a coupling, either adhesive 72 or insert 74, apply to second electrode apparatus 96 as well. Consequently, second electrode apparatus 96 need not be described in detail herein.

Double-ring configuration 98 further includes a spacer 104, of which two are shown, coupled to each of electrode 22 and second electrode 99 for maintaining a physical separation between first and second electrodes 22 and 99, respectively. Spacer 104 includes a first cylindrical portion 106, a second cylindrical portion 108, and a tubular portion 110. First cylindrical portion 106 includes a first tip 112. Similarly, second cylindrical portion 108 includes a second tip 114. First tip 112 is secured in a first one of holes 40, designated first hole 40', in electrode 22.

Likewise second tip 114 is secured via press-fit and/or bonding, in a second one of holes 40, designated second hole 40", in second electrode 99. First and second cylindrical portions 106 and 108, respectively, are subsequently press-fit into opposing ends of tubular portion 110. In this manner, electrode 22 and second electrode 99 are physically separated.

In a preferred embodiment, first and second cylindrical portions 106 and 108 are rigid members formed out of rigid conductive or non-conductive materials, for providing structural stability. Tubular portion 110 is formed out of elastomeric conductive or non-conductive material thus providing a comfortable contact surface for the user.

Spacer 104, i.e., first and second cylindrical portions 106 and 108 and tubular portion 110, are either electrically conductive or non-conductive depending upon the desired application. For example, electrical contacts 24 and 100 may be coupled to a common source of electricity, typically a controller allowing for adjustment of current (not shown), and receive the same signal. As such, spacer 104 would desirably be conductive to enable a current path between first and second electrode apparatuses 20 and 96, respectively. Alternatively, the source of electricity may have two outputs so that each of first and second electrode apparatuses 20 and 96 may receive independent signals. As such, spacer 104 would desirably be non-conductive so that a current path cannot be enabled between first and second electrode apparatuses 20 and 96, respectively.

Figure 6:
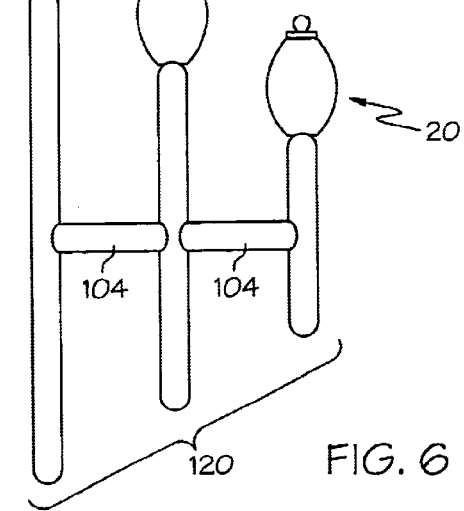
FIG. 6 shows a side view of the electrode apparatus of FIG. 1 coupled with a second and a third electrode apparatus to form a triple-ring configuration.

FIG. 6 shows a side view of electrode apparatus 20 coupled with a second electrode apparatus 116, and coupled with a third electrode apparatus 118 to form a triple-ring configuration 120. Electrode apparatus 20, second electrode apparatus 116, and third electrode apparatus 118 are physically separated by spacers 104.

The electrode apparatus of the present invention need not be limited to a single electrode apparatus 20 (FIG. 1) or to double-ring configuration 98. Rather, a number of electrodes may be employed to administer the desired amount of electrical stimulation along, for example, the shaft of a penis. Nor does the diameter of each of apparatuses 20, 116, and 118 in ring-shaped configuration (FIG. 1) need to be the same. Rather, as exemplified in FIG. 6, each of electrode apparatus 20, second electrode 116, and third electrode apparatus 118 may be trimmed (as discussed above) to form different diameter elements, for the purpose of comfortably fitting along the penis. In addition, the lengths of first and second cylindrical portions 106 and 108, and tubular portion 110, may be adjusted to function cooperatively in triple-ring configuration 120.

Figure 7:
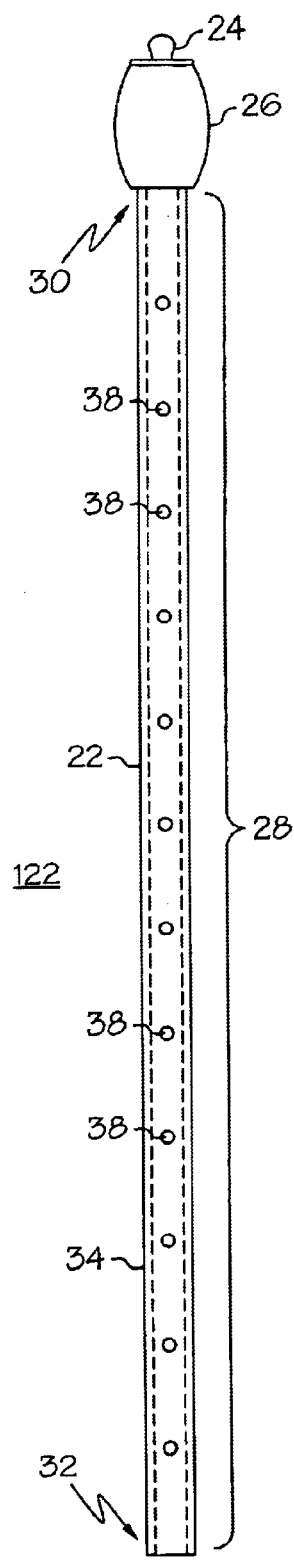
FIG. 7 shows a perspective view of an electrode apparatus in accordance with an alternative embodiment of the present invention.
Figure 8:
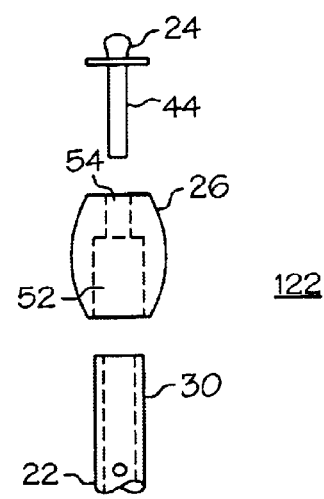
FIG. 8 shows a partial exploded view of the electrode apparatus of FIG. 4.

Referring to FIGS. 7–8, FIG. 7 shows a perspective view of an electrode apparatus 122 in accordance with an alternative embodiment of the present invention. FIG. 8 shows a partial exploded view of electrode apparatus 122. Electrode apparatus 122 includes electrode 22, electrical contact 24, non-conductive sheath 26, and openings 38 disposed along length 28 of electrode 22, and discussed in detail above in connection with FIGS. 1–2.

To fabricate electrode apparatus 122, first end 30 of electrode apparatus 122 is press-fit into first interior portion 52 of non-conductive sheath 26. In addition, insert end 44 of electrical contact 24 is inserted through second interior portion 54 of sheath 26 and press-fit through first end 30 and into interior passage 36 of electrode 22. Encapsulating tube 84 (FIG. 3), sized to enclose length 28 of electrode 22, is temporarily placed about exterior surface 34 of electrode 22 so that open end 90 (FIG. 3) of encapsulating cylinder 84 is positioned about second end 32. Electrolytic gel 88 (FIG. 3) is forced through second end 32 into interior passage 36 (FIG. 2) using injection element 86 (FIG. 3). When interior passage 36 is full, as viewed through the translucent encapsulating cylinder 84, encapsulating cylinder is removed from electrode 22, and electrode apparatus 122 can be placed into use.

Electrode apparatus 122 is particularly configured for insertion in bodily orifices, such as the urethra and anus. Openings 38 facilitate a leakage of electrolytic gel 88 from interior passage 36 to exterior surface 34 when in use to provide lubrication during insertion and so that electrical energy is evenly distributed on body tissues and the development of hot spots is largely prevented.

Figure 9:
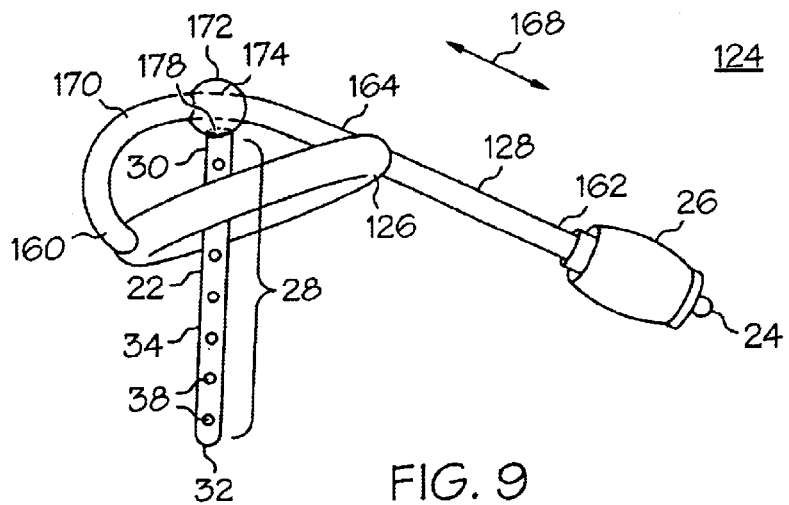
FIG. 9 shows a perspective view of an electrode apparatus in accordance with another alternative embodiment of the present invention.
Figure 10:
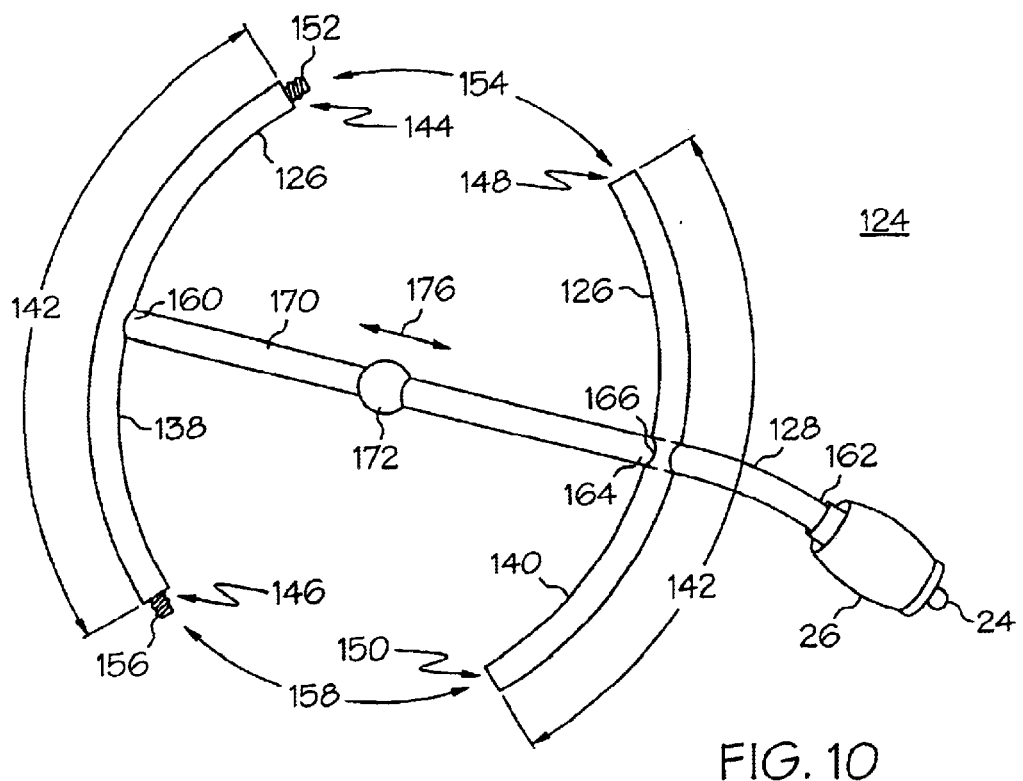
FIG. 10 shows a top view of the electrode apparatus of FIG. 9 in a partially dissembled form.

Referring to FIGS. 9–10, FIG. 9 shows a perspective view of an electrode apparatus 124 in accordance with another alternative embodiment of the present invention. FIG. 10 shows a top view of electrode apparatus 124 in a partially dissembled form. Electrode apparatus 124 includes electrode 22, electrical contact 24, non-conductive sheath 26, and openings 38 disposed along length 28 of electrode 22, and discussed in detail above in connection with FIGS. 1–2. Electrode apparatus 124 further includes a flexible ring 126 and an electrically conductive section 128.

Flexible ring 126 includes a first ring portion 138 and a second ring portion 140. First ring portion 138 exhibits a second length 142, and a first ring end 144 and a second ring 146 located at opposite ends of first ring portion 138. Similarly, second ring portion 140 exhibits second length 142, and a third ring end 148 and a fourth ring end 150 located at opposite ends of second ring portion 140.

A first coupling 152 is configured for removable attachment of first ring end 144 of first ring portion 138 to third ring end 148 of second ring portion 140, as indicated by a first bi-directional arrow 154. A second coupling 156 is configured for removable attachment of second ring end 146 of first ring portion 138 to fourth ring end 150 of second ring portion 140, as indicated by a second bi-directional arrow 158. In operation, first, second, third, and fourth ring ends 144, 146, 148, and 150, respectively, may be trimmed to the appropriate length so that when the respective ring ends are coupled, as described above, electrode apparatus 124 comfortably and securely fits about the penis.

Flexible ring 126 is fabricated from an elastomeric material such as silicone, fluorolastomer, or neoprene, such material being comfortable, and readily cleanable. Flexible ring 126 may be made either conductive or non-conductive. Flexible ring 126 is flexible so that ring 126 can adapt to the particular anatomy upon which it will be worn. In particular, flexible ring 126 is configured to fit about the corona of the penis, the corona demarcating where the glans and the shaft of the penis join.

Electrically conductive section 128 has a first section end 160, a second section end 162, and an intermediate portion 164 between first and second section ends 160 and 162, respectively. First section end 160 is coupled to and extends from first ring portion 138 of flexible ring 126 and intermediate portion 164 extends through a hole 166 extending through second ring portion 140 of flexible ring 126. Hole 166 is sized to allow intermediate portion 164 of electrically conductive section 128 to slide within hole 166, as indicated by a bidirectional arrow 168. Electrical contact 24 is in electrical communication with second section end 162 of electrically conductive section 128.

Electrically conductive section 128 is desirably fabricated from an elastomeric material such as silicone, fluorolastomer, or neoprene for comfort and cleanability and is made conductive along the length of section 128 by embedding carbon particles in the elastomeric material during fabrication. Alternatively, electrically conductive section 128 may be fabricated from other pliable conductive materials such as conductive ceramic, metals, twisted or braided wires, and such. In addition, electrically conductive section 128 is flexible so that section 128 can adapt to the particular anatomy upon which it will be worn. In particular, a region 170 of electrically conductive section 128 between first section end 160 and intermediate portion 164 is configured to fit over and contact the glans and the urethral opening (not shown) of the penis.

Electrode apparatus 124 further includes a conductive sphere 172 coupled to region 170 between first section end 160 and intermediate portion 164 of electrically conductive section 128. Conductive sphere 172 is in electrical communication with electrically conductive section 128. Conductive sphere 172 includes an interior passage 174 (represented by hidden lines) through which region 170 of electrically conductive section 128 is routed. Interior passage 174 is sized such that conductive sphere 172 is slideable along electrically conductive section 128, as denoted by a bidirectional arrow 176.

Conductive sphere 172 may be constructed of silicone composite conductive material, conductive ceramic, conductive metals, and so forth that move freely along electrically conductive section 128. Conductive sphere 172 is utilized to impart concentrated, or focused, electrical energy to the urethral opening of the penis.

First end 30 of electrode 22 is supported by region 170 of electrically conductive section 128. In particular, first end 30 of electrode 22 is inserted and secured by press-fitting and/or bonding into a second interior passage 178 of conductive sphere 138, as denoted by dashed lines.

In use, encapsulating tube 84 (FIG. 3), sized to enclose length 28 of electrode 22, is temporarily placed about exterior surface 34 of electrode 22 so that open end 90 (FIG. 3) of encapsulating cylinder 84 is positioned about second end 32. Electrolytic gel 88 (FIG. 3) is forced through second end 32 into interior passage 36 (FIG. 2) using injection pump 86 (FIG. 3). When interior passage 36 is full, as viewed through the translucent encapsulating cylinder 84, encapsulating cylinder is removed from electrode 22, and electrode apparatus 124 can be placed into use.

Electrode 22 of electrode apparatus 124 is particularly configured to impart concentrated electrical energy within the urethra. However, openings 38 facilitate a leakage of electrolytic gel 88 from interior passage 36 to exterior surface 34 when in use to provide lubrication during insertion and so that the concentrated electrical energy is evenly distributed on body tissues and the development of hot spots is largely prevented.

Figure 11:
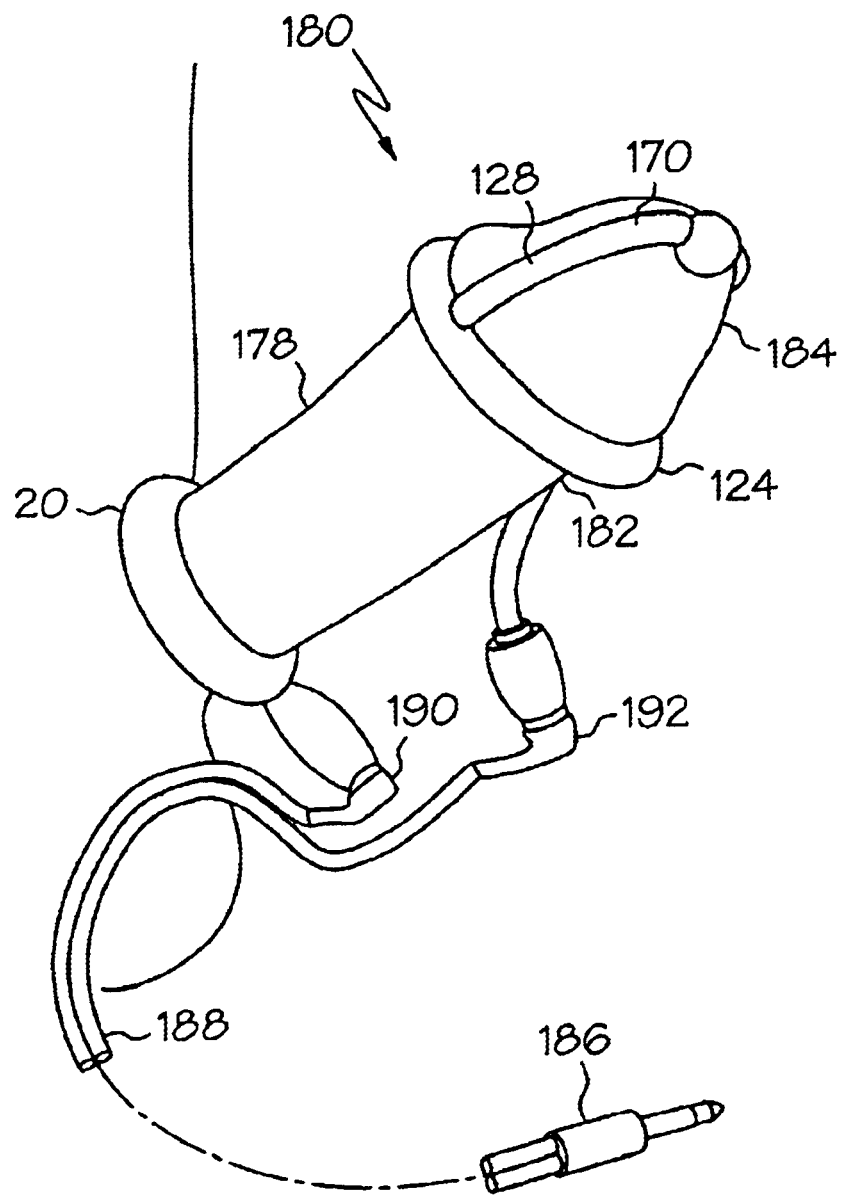
FIG. 11 shows a diagram of the electrode apparatuses of FIGS. 1 and 9 in use.

FIG. 11 shows a diagram of electrode apparatus 20 and electrode apparatus 124 in use. As shown, electrode apparatus 20 is worn about a shaft 178 of a penis 180. Electrode apparatus 124 is worn so that flexible ring 126 fits about a corona 182 of the penis, corona 182 demarcating where a glans 184 and shaft 178 of penis 180 join. In addition, region 170 of electrically conductive section 128 fits over and contacts glans 184 and the urethral opening (not shown) of penis 180. Conductive sphere 172 fits over the urethral opening (not shown) of penis 180 and electrode 22 (FIG. 9) fits within the urethra (not shown). Each of electrical contacts 24 (FIG. 1 and FIG. 9) of electrode apparatuses 20 and 124 are connected to a source of electricity, typically a controller allowing for adjustment of current (not shown). The controller will typically include a jack 186 and a wire 188 connected to jack 186. Wire 188 will typically terminate with a first connector 190 configured for attachment to electrical contact 24 of electrode apparatus 20, and a second connector 192 for attachment to electrical contact 24 of electrode apparatus 124 for completing the electrical path through penis 42.

In summary, the present invention teaches an electrode apparatus for the electrical stimulation of the penile glans, corona, and urethral tissue to induce erection and/or orgasm. The electrode apparatus is comfortable to wear due to the ability to adjust the length of the electrode and its flexibility when in use. Furthermore, the leakage of the electrolytic gel from the electrode when in use provides lubrication and enables an even distribution of electrical contact between the apparatus and tissue so that electrical energy is evenly distributed on body tissues and the development of hot spots is largely prevented.

Although the preferred embodiments of the invention have been illustrated and described in detail, it will be readily apparent to those skilled in the art that various modifications may be made therein without departing from the spirit of the invention or from the scope of the appended claims.

What is claimed is:

1. An electrode apparatus comprising:

an electrode exhibiting a length, and having first and second ends located at opposite ends of said length, an exterior surface, an interior passage, and openings disposed along said length and extending from said exterior surface to said interior passage, said interior passage being configured for placement of a quantity of an electrolytic gel, and said openings facilitating a leakage of said electrolytic gel from said interior passage to said exterior surface of said electrode when said electrode apparatus is in use;

an electrical contact;

a non-conductive sheath surrounding a portion of said electrical contact and retaining said electrical contact in electrical communication with said electrode an encapsulating cylinder in temporary placement about said exterior surface of said electrode, said encapsulating cylinder having an open end positioned about said first end of said electrode; and an injection element configured to contain said quantity of electrolytic gel, wherein an outlet of said injection element is positioned at said open end of said encapsulating cylinder and said electrolytic gel is forced through said first end and into said interior passage of said electrode, and prior to use, said encapsulating cylinder is removed from said exterior surface of said electrode.

2. An electrode apparatus comprising:

an electrode exhibiting a length, and having first and second ends located at opposite ends of said length, an exterior surface, an interior passage, and openings disposed along said length and extending from said exterior surface to said interior passage;

a coupling for attaching said first end to said second end to retain said electrode in a ring-shaped configuration;

an electrical contact; and a non-conductive sheath surrounding a portion of said electrical contact and retaining said electrical contact in electrical communication with said electrode.

3. An electrode apparatus as claimed in claim 2 wherein said openings are arranged along an inside circumference of said electrode when said electrode is oriented in said ring-shaped configuration.

4. An electrode apparatus as claimed in claim 2 wherein said coupling is an adhesive for non-removable attachment of said first end to said second end.

5. An electrode apparatus as claimed in claim 4 wherein said adhesive is a cyanoacrylate adhesive.

6. An electrode apparatus as claimed in claim 2 wherein said coupling is an insert having a first insert end positioned in said interior passage at said first end of said electrode and having a second insert end positioned in said interior passage at said second end of said electrode for removable attachment of said first end to said second end.

7. An electrode apparatus as claimed in claim 6 wherein said insert has an uneven exterior surface for providing surface resistance between said insert and said interior passage of said electrode.

8. An electrode apparatus comprising:
an electrode exhibiting a length, and having first and second ends located at opposite ends of said length, an exterior surface, an interior passage, and openings disposed along said length and extending from said exterior surface to said interior passage;
an electrical contact;
a non-conductive sheath surrounding a portion of said electrical contact and retaining said electrical contact in electrical communication with said electrode; and
a conductive member bonded to said electrode and installed in said non-conductive sheath, said conductive member being in electrical communication with said electrical contact.

9. An electrode apparatus as claimed in claim 8 wherein said non-conductive sheath includes a bore, said bore having a first interior portion exhibiting a first inner diameter, and a second interior portion exhibiting a second inner diameter that is less than said first inner diameter, said first and second interior portions being axially aligned and contiguous, said conductive member being press-fit into said first interior portion, and an end of said electrical contact being inserted through said second interior portion and into said first interior portion to contact said conductive member.

10. An electrode apparatus as claimed in claim 8 wherein:
said conductive member is a conductive tubular member;
said electrode further includes an aperture located on said length and extending from said exterior surface to said interior passage, said conductive tubular member is bonded to said electrode about said aperture; and
said electrode apparatus further comprises a rigid conductive dowel disposed in said electrode and extending from said aperture to seat in said conductive tubular member for ensuring electrical continuity between said electrical contact and said electrode.

11. An electrode apparatus comprising:
an electrode exhibiting a length, and having first and second ends located at opposite ends of said length, an exterior surface, an interior passage, and openings disposed along said length and extending from said exterior surface to said interior passage;
an electrical contact; and
a non-conductive sheath surrounding a portion of said electrical contact and retaining said electrical contact in electrical communication with said electrode, said non-conductive sheath including a bore, said bore having a first interior portion exhibiting a first inner diameter, and a second interior portion exhibiting a second inner diameter that is less than said first inner diameter, said first and second interior portions being axially aligned and contiguous, said first end of said electrode being press-fit into said first interior portion, and an end of said electrical contact being inserted through said second interior portion and press-fit into said first end of said electrode located in said first interior portion.

12. An electrode apparatus comprising:
a first electrode exhibiting a length, and having first and second ends located at opposite ends of said length, an exterior surface, an interior passage, and openings disposed along said length and extending from said exterior surface to said interior passage;
an electrical contact;
a non-conductive sheath surrounding a portion of said electrical contact and retaining said electrical contact in electrical communication with said electrode;
a first coupling for attaching said first end to said second end to retain said first electrode in a ring-shaped configuration;
a second electrode exhibiting a second length, and having third and fourth ends located at opposite ends of said second length, a second exterior surface, a second interior passage, and second openings disposed along said length and extending from said second exterior surface to said second interior passage;
a second electrical contact;
a second non-conductive sheath surrounding a second portion of said second electrical contact and retaining said second electrical contact in electrical communication with said second electrode;
a second coupling for attaching said third end to said fourth end to retain said second electrode in said ring-shaped configuration; and
a spacer coupled to each of said first and second electrodes for maintaining a physical separation between said first and second electrodes.

13. An electrode apparatus comprising:
a first electrode exhibiting a length, and having first and second ends located at opposite ends of said length, an exterior surface, an interior passage, and openings disposed along said length and extending from said exterior surface to said interior passage;
an electrical contact;
a non-conductive sheath surrounding a portion of said electrical contact and retaining said electrical contact in electrical communication with said electrode;
a second electrode exhibiting a second length, and having third and fourth ends located at opposite ends of said second length, a second exterior surface, a second interior passage, and second openings disposed along said length and extending from said second exterior surface to said second interior passage;
a second electrical contact;
a second non-conductive sheath surrounding a second portion of said second electrical contact and retaining said second electrical contact in electrical communication with said second electrode; and
a conductive spacer coupled to each of said first and second electrodes for maintaining a physical separation between said first and second electrodes.

14. An electrode apparatus comprising:
a first electrode exhibiting a length, and having first and second ends located at opposite ends of said length, an exterior surface, an interior passage, and openings disposed along said length and extending from said exterior surface to said interior passage, and said first electrode including a first hole;
an electrical contact;
a non-conductive sheath surrounding a portion of said electrical contact and retaining said electrical contact in electrical communication with said electrode;
a second electrode exhibiting a second length, and having third and fourth ends located at opposite ends of said second length, a second exterior surface, a second interior passage, and second openings disposed along said length and extending from said second exterior surface to said second interior passage, and said second electrode including a second hole;

a second electrical contact;

a second non-conductive sheath surrounding a second portion of said second electrical contact and retaining said second electrical contact in electrical communication with said second electrode; and a spacer coupled to each of said first and second electrodes for maintaining a physical separation between said first and second electrodes, a first tip of said spacer being secured in said first hole of said first electrode, and a second tip of said spacer being secured in said second hole of said second electrode.

15. An electrode apparatus comprising:

a first electrode exhibiting a length, and having first and second ends located at opposite ends of said length, an exterior surface, an interior passage, and openings disposed along said length and extending from said exterior surface to said interior passage;

an electrical contact;

a non-conductive sheath surrounding a portion of said electrical contact and retaining said electrical contact in electrical communication with said electrode;

a second electrode exhibiting a second length, and having third and fourth ends located at opposite ends of said second length, a second exterior surface, a second interior passage, and second openings disposed along said length and extending from said second exterior surface to said second interior passage;

a second electrical contact;

a second non-conductive sheath surrounding a second portion of said second electrical contact and retaining said second electrical contact in electrical communication with said second electrode; and a spacer coupled to each of said first and second electrodes for maintaining a physical separation between said first and second electrodes, said spacer including:
 a first cylindrical portion having said first tip;
 a second cylindrical portion having said second tip; and
 a tubular portion, said first and second cylindrical portions being press-fit into opposing ends of said tubular portion.

16. An electrode apparatus comprising:

an electrode exhibiting a length, and having first and second ends located at opposite ends of said length, an exterior surface, an interior passage, and openings disposed along said length and extending from said exterior surface to said interior passage;

an electrical contact;

a non-conductive sheath surrounding a portion of said electrical contact and retaining said electrical contact in electrical communication with said electrode a flexible ring; and a conductive section having a first section end, a second section end, and an intermediate portion between said first and second section ends, said first section end coupled to and extending from said flexible ring, said intermediate portion extending through a hole in said flexible ring, and said first end of said electrode being supported by a region of said electrically conductive section between said first end and said intermediate portion.

17. An apparatus as claimed in claim 16 wherein said flexible ring includes:

a first ring portion exhibiting a second length, a first ring end, and a second ring end, said first section end of said conductive section being coupled to said first ring portion at an approximate mid-point of said second length of said first ring portion; and a second ring portion exhibiting said second length, a third ring end, and a fourth ring end, said intermediate portion of said conductive section extending through said hole at said approximate mid-point of said second length of said second ring portion;

said electrode apparatus further comprises:
 a first coupling for removably attaching said first ring end of said first ring portion to said third ring end of said second ring portion; and
 a second coupling for removably attaching said second ring end of said first ring portion to said fourth ring end of said second ring portion, said first and second couplings serving to retain a ring-shaped configuration of said flexible ring.

18. An electrode apparatus comprising:

an electrode exhibiting a length, and having first and second ends located at opposite ends of said length, an exterior surface, an interior passage, and openings disposed along said length and extending from said exterior surface to said interior passage, said interior passage being configured for placement of a quantity of an electrolytic gel, and said openings facilitating a leakage of said electrolytic gel from said interior passage to said exterior surface of said electrode when said electrode apparatus is in use;

a coupling for attaching said first end to said second end to retain said electrode in a ring-shaped configuration so that said openings are arranged along an inside circumference of said electrode when said electrode is oriented in said ring-shaped configuration;

an electrical contact; and a non-conductive sheath surrounding a portion of said electrical contact and retaining said electrical contact in electrical communication with said electrode.

19. An electrode apparatus as claimed in claim 18 further comprising:

an encapsulating cylinder in temporary placement about said exterior surface of said electrode, said encapsulating cylinder having an open end locatable about either of said first and second ends of said electrode prior to attachment of said coupling to said first and second ends; and an injection element configured to contain said quantity of electrolytic gel, wherein an outlet of said injection element is positioned in said open end of said encapsulating cylinder and said electrolytic gel is forced through said either of said first and second ends and into said interior passage of said electrode, and prior to attachment of said coupling, said encapsulating cylinder is removed from said exterior surface of said electrode.

20. An electrode apparatus as claimed in claim 18 wherein said coupling is an insert having a first insert end positioned in said interior passage at said first end of said electrode and having a second insert end positioned in said interior passage at said second end of said electrode for removable attachment of said first end to said second end.

21. An electrode apparatus as claimed in claim 18 wherein said electrode is a first electrode, and said electrode apparatus further comprises:

a second electrode exhibiting a second length, having third and fourth ends located at opposite ends of said second length, a second exterior surface, a second interior passage, and second openings disposed along said length and extending from said second exterior surface to said second interior passage, said second interior passage being configured for placement of a second quantity of said electrolytic gel, and said second openings facilitating a leakage of said second quantity of said electrolytic gel from said second interior passage to said second exterior surface of said second electrode when said electrode apparatus is in use;

a second coupling for attaching said third end to said fourth end to retain said second electrode in said ring-shaped configuration so that said second openings are arrange along an inside circumference of said second electrode when said second electrode is oriented in said ring-shaped configuration;

a second electrical contact;

a second non-conductive sheath surrounding a second portion of said second electrical contact and retaining said second electrical contact in electrical communication with said second electrode; and a spacer coupled to each of said first and second electrodes for maintaining a physical separation between said first and second electrodes.

* * * * *